US009207300B2

(12) United States Patent
Bi et al.

(10) Patent No.: US 9,207,300 B2
(45) Date of Patent: Dec. 8, 2015

(54) AUTOMATIC SYSTEM FOR TIMING IN IMAGING

(71) Applicants: Xiaoming Bi, Aurora, IL (US); Sven Zuehlsdorff, Westmont, IL (US); Christopher Glielmi, Hoboken, NJ (US); Ning Jin, Powell, OH (US)

(72) Inventors: Xiaoming Bi, Aurora, IL (US); Sven Zuehlsdorff, Westmont, IL (US); Christopher Glielmi, Hoboken, NJ (US); Ning Jin, Powell, OH (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 169 days.

(21) Appl. No.: 13/964,165

(22) Filed: Aug. 12, 2013

(65) Prior Publication Data
US 2014/0121496 A1 May 1, 2014

Related U.S. Application Data

(60) Provisional application No. 61/718,731, filed on Oct. 26, 2012.

(51) Int. Cl.
 A61B 5/055 (2006.01)
 G01R 33/54 (2006.01)
 A61B 5/00 (2006.01)
 G01R 33/563 (2006.01)
 G01R 33/567 (2006.01)
 A61B 5/0456 (2006.01)

(52) U.S. Cl.
 CPC ............ *G01R 33/543* (2013.01); *A61B 5/0044* (2013.01); *A61B 5/055* (2013.01); *A61B 5/7292* (2013.01); *G01R 33/5673* (2013.01); *G01R 33/56325* (2013.01); *A61B 5/0456* (2013.01)

(58) Field of Classification Search
 CPC .... A61B 5/0044; A61B 5/0456; A61B 5/055; A61B 5/7292; G01R 33/543; G01R 33/56325; G01R 33/5673
 See application file for complete search history.

(56) References Cited

U.S. PATENT DOCUMENTS

| 2009/0290776 A1 | 11/2009 | Sun et al. |
| 2010/0145182 A1 | 6/2010 | Schmidt et al. |
| 2010/0268066 A1 | 10/2010 | Rehwald et al. |
| 2012/0121152 A1 | 5/2012 | Lu et al. |

OTHER PUBLICATIONS

Matthias Stuber et al., "Submillimeter Three-dimensional Coronary MR Angiography with Real-time Navigator Correction: Comparison of Navigator Locations",Radiology 1999; 212:579-587.

(Continued)

*Primary Examiner* — Jonathan Cwern
(74) *Attorney, Agent, or Firm* — Peter R. Withstandley (57) ABSTRACT

An imaging system automatically determines a cardiac timing parameter for acquiring a cardiac image in a heart phase. An interface receives data identifying a heart image orientation for image acquisition. A repository of data associates, for acquisition of an image in a particular heart phase, different image orientations with corresponding different data items identifying respective corresponding particular acquisition points within an individual heart cycle relative to a start point of the heart cycle. An acquisition timing processor determines from the repository of data, a particular acquisition point within an individual heart cycle relative to the start point of the heart cycle, in response to the received data identifying the heart image orientation and uses the determined particular acquisition point to provide a synchronization signal for triggering acquisition of an image at the particular heart phase.

14 Claims, 9 Drawing Sheets

(56) References Cited

OTHER PUBLICATIONS

Harald Seifarth, et al., "Optimal Systolic and Diastolic Reconstruction Windows for Coronary CT Angiography Using Dual-Source CT", American Journal of Roentgenology, 2007; 189: 1317-1323.

X. Bi et al., "Optimal Selection of the subject-specific data acquisition window for coronary MRA", Proc. Intl. Soc. Mag. Reson. Med. vol. 14, p. 2163, 2006.

X. Bi et al., "A fully automated selection of the optimal data acquisition window in coronary MRA eliminating the need for user-interaction", Proceedings of the International Society for Magnetic Resonance in Medicine, 15th Scientific Meeting and Exhibition. 2007.

AUTOMATIC SYSTEM FOR TIMING IN IMAGING

This application claims priority to U.S. provisional application Ser. No. 61/718,731 filed Oct. 26, 2012, which is incorporated herein by reference in its entirety.

FIELD OF THE INVENTION

This invention concerns an imaging system for automatic determination of a cardiac timing parameter for acquiring a cardiac image in a desired heart phase.

BACKGROUND OF THE INVENTION

Despite improvement in hardware, modern imaging methods including MRI are sensitive to motion of imaging objects such as organs. The sources of motion include physiological motion from heart beating, respiratory motion, as well as voluntary and involuntary movement of patients during imaging procedures. Such motion leads to compromised image quality. In cardiac MRI for example, motion may lead to blurring of heart images, ghosting artifacts of the chest wall and/or other moving organs, or heterogeneous signal distribution across homogeneous tissue, e.g., a myocardium and blood pool. Consequently, the motion may result in non-diagnostic quality images or even false positive or negative findings.

Increased imaging speed improves patient comfort and imaging throughput and reduces the impact of motion on images. State-of-the-art MR scanners are equipped with a strong magnetic gradient system for fast switching of gradient pulses within the limits of peripheral nerve stimulation for increased imaging speed. High density coil arrays are used providing advanced sampling and reconstruction methods for accelerated imaging by under-sampling imaging data. While these features may improve image quality and consistency of results, the degree of motion is still larger than a typical imaging voxel size and the speed of motion is significant compared to image acquisition time in many applications and causes degraded image quality.

Imaging a moving heart has been typically performed by synchronizing data acquisition to an electrocardiogram (ECG) signal. This ensures imaging data may be consistently acquired in the same cardiac phase with same degree of cardiac motion, or acquired in a specific time period (typically mid-diastole or end-systole) comprising minimal cardiac motion. Precise motion control is desirable for many cardiac applications that require high spatial resolution or homogeneous signal. For example, visualization of coronary artery lumen and/or a coronary vessel wall requires submillimeter spatial resolution while cardiac motion may be of the order of a centimeter. Tissue characterization relies on subtle difference in MR luminance signal intensity between normal and pathological myocardium and signal intensity may be skewed by motion.

Further, parametric mapping methods (T1, T2, T2* based method) require motion control to derive accurate pixel-wise relaxation parameters. These methods require accurate selection of an image acquisition trigger time to minimize adverse impact on image results from cardiac motion. A system according to invention principles addresses deficiencies of the known imaging methods in imaging in the presence of motion and related problems.

SUMMARY OF THE INVENTION

Figure 2:
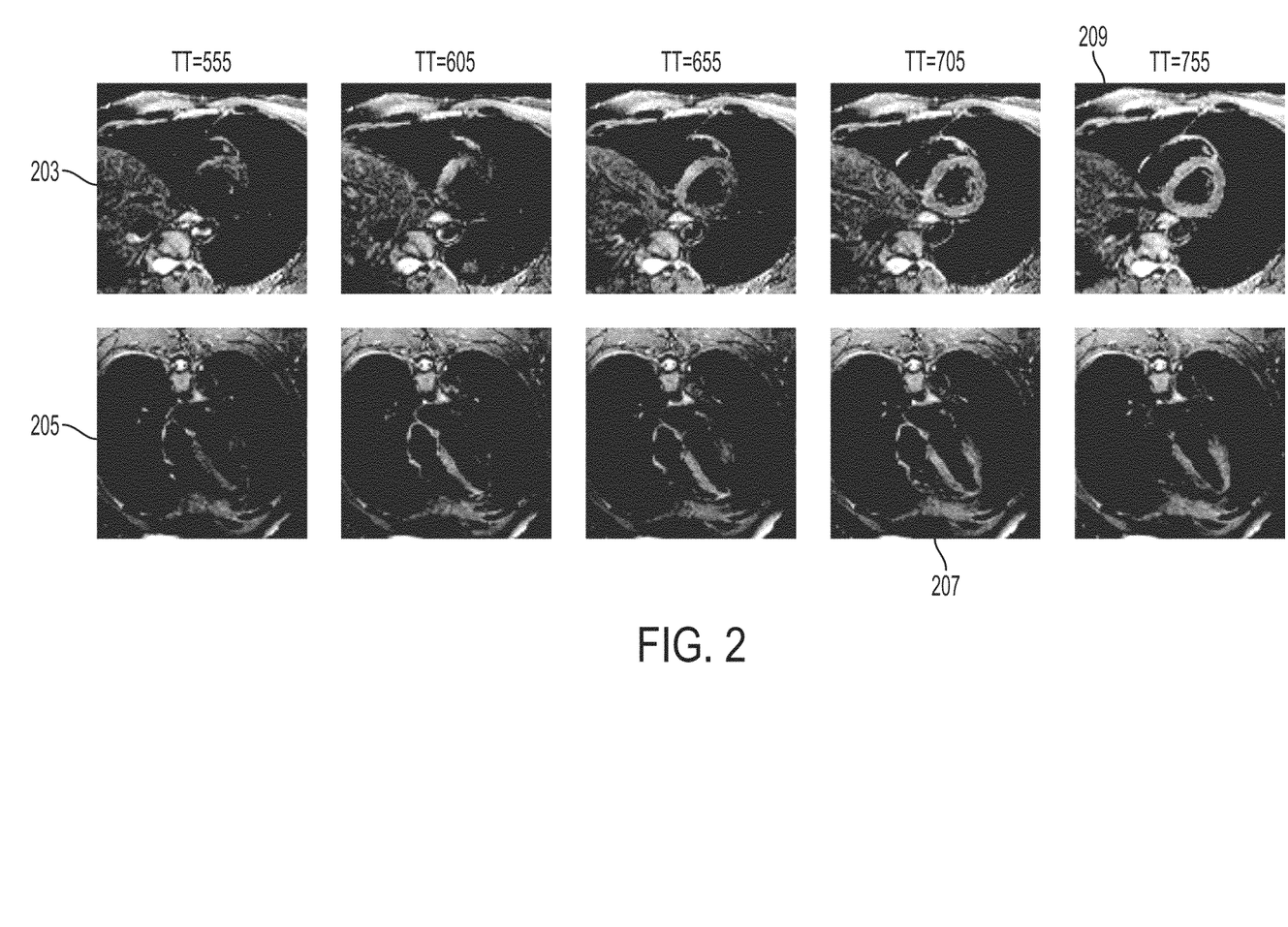
FIG. 2 shows images from a healthy patient in short-axis and four-chamber views using a dark-blood prepared Turbo Spin-Echo (TSE) sequence.

FIG. 2 shows known image acquisition short-axis (row 203) and four-chamber (row 205) views from a healthy patient acquired using a clinical dark-blood turbo spin-echo sequence showing that image quality depends on the selection of trigger time, and the optimal acquisition time varies for different views even for the same patient. Trigger time (TT) refers to delay time between an electrocardiogram RR wave and acquisition of center k-space lines. The images show dependence of image quality on the selection of TT in both views, as well as difference in optimal TT in short-axis and four-chamber views of the same patient, according to invention principles. Optimal image 207 for the four chamber view is acquired at TT=705 ms whereas optimal image 209 for the short axis view is acquired at TT=755 ms, for example. An MR imaging system automates selection of patient-specific, orientation-dependent optimal timing parameters in order to achieve consistent, operator-independent image quality with minimal motion artifacts in cardiac imaging, for example. An imaging system automatically determines a cardiac timing parameter for acquiring a cardiac image in a desired heart phase. An interface receives data identifying a heart image orientation for image acquisition. A repository of data associates, for acquisition of an image in a particular heart phase, different image orientations with corresponding different data items identifying respective corresponding particular acquisition points within an individual heart cycle relative to a start point of the heart cycle. An acquisition timing processor determines from the repository of data, a particular acquisition point within an individual heart cycle relative to the start point of the heart cycle, in response to the received data identifying the heart image orientation and uses the determined particular acquisition point to provide a synchronization signal for triggering acquisition of an image at the particular heart phase.

DETAILED DESCRIPTION OF THE INVENTION

An MR imaging system according to invention principles automates selection of patient-specific, orientation-dependent optimal timing parameters in order to achieve consistent, operator-independent image quality with minimal motion artifacts in cardiac imaging, for example. The system automates selection of scanning views and imaging field-of-view, in providing automated cardiac scans with patient-specific, operator-independent settings for optimal image quality.

The degree of cardiac motion and required synchronization vary substantially among patients. Known empirical equations (e.g., equation trigger delay=$[(t_{RR}-350)\times 0.3]+350$) do not describe patient-specific cardiac motion. The inventors have advantageously recognized that for a specific patient, cardiac motion depends on imaging orientation since activation of myocardium in different parts of the heart varies and may not be correlated. Such lack of correlation is shown in FIG. 2. This is more problematic in patients with cardiac dyssynchrony. In known clinical procedure, selection of timing for cardiac MRI imaging data acquisition is typically based on one of the following methods, 1) estimating a timing value based on an empirical equation or 2) identifying quiescent cardiac phases with minimal cardiac motion by examining specific cine images (mostly in a 4-chamber view of the heart). Both methods of timing selection are problematic. Method 1) is not specific to a given patient or imaging orientation and method 2) is also not specific to imaging orientation and is highly operator dependent.

It is known that view planning for cardiac MRI can be automated from a static 3D imaging volume or a stack of 2D images. It is also known that an imaging field-of-view in cardiac MRI may be automatically determined and image acquisition pulse sequence timing parameters may be determined for optimal blood signal suppression for dark-blood and inversion preparation. Combination of these methods facilitates automating image plane determination and reduces operator dependence. However, known systems fail to support automatic selection of optimal timing parameters for minimizing cardiac motion induced artifacts.

Figure 1:
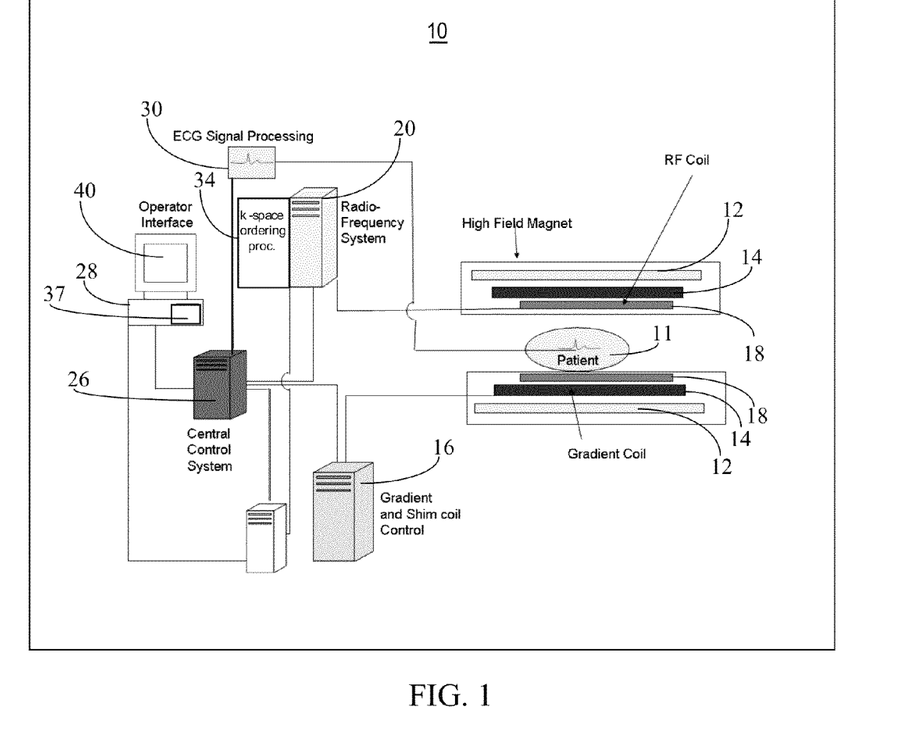
FIG. 1 shows an imaging system for automatic determination of a cardiac timing parameter for acquiring a cardiac image in a desired heart phase, according to invention principles.

FIG. 1 shows imaging system 10 for automatic determination of a cardiac timing parameter for acquiring a cardiac image in a desired heart phase. System 10 advantageously employs a 4D (or time-resolved 3D) volume instead of a static 3D volume, in providing an automated process for cardiac magnetic resonance imaging, including scan view planning, field-of-view determination and patient- and view-specific optimal timing selection. System 10 comprises an automated MR image data acquisition system for automated cardiac examinations according to some embodiments of the present invention.

In system 10, magnet 12 creates a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shimming and pulse sequence control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coils 18, which in response produce magnetic field pulses which rotate the spins of the protons in the imaged body 11 by ninety degrees or by one hundred and eighty degrees for so-called "spin echo" imaging, or by angles less than or equal to 90 degrees for so-called "gradient echo" imaging. Pulse sequence control module 16 in conjunction with RF module 20 as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coils 18 receives MR signals, i.e., signals from the excited protons within the body as they return to an equilibrium position established by the static and gradient magnetic fields. The MR signals are detected and processed by a detector within RF module 20 and k-space component processor unit 34 to provide image representative data to an image data processor in central control unit 26. ECG synchronization signal generator 30 provides ECG signals used for pulse sequence and imaging synchronization. A two or three dimensional k-space storage array of individual data elements in unit 34 stores corresponding individual frequency components comprising an MR dataset.

Computer 28 (or at least one processing device in one or more other units of system 10 in a different embodiment) includes an interface, repository and image data processor including an acquisition timing processor. The interface receives data identifying a heart image orientation for image acquisition. The repository includes data associating, different image orientations with corresponding different data items identifying respective corresponding particular acquisition points within an individual heart cycle relative to a start point of the heart cycle. The repository association data is used for acquisition of an image in a particular heart phase. The acquisition timing processor determines from the repository of data, a particular acquisition point within an individual heart cycle relative to the start point of the heart cycle, in response to the received data identifying the heart image orientation. Also the acquisition timing processor uses the determined particular acquisition point to provide a synchronization signal for triggering acquisition of an image at the particular heart phase. The image data processor uses multiple sets of volume image data for determining corresponding respective multiple two dimensional (2D) images within a volume at the heart image orientation. Further, the image data processor determines at least one of, (a) particular 2D image of the multiple 2D images and (b) a particular time in the heart cycle relative to a start of the heart cycle, in response to correlation of successive images of the plurality of 2D images.

Figure 3:
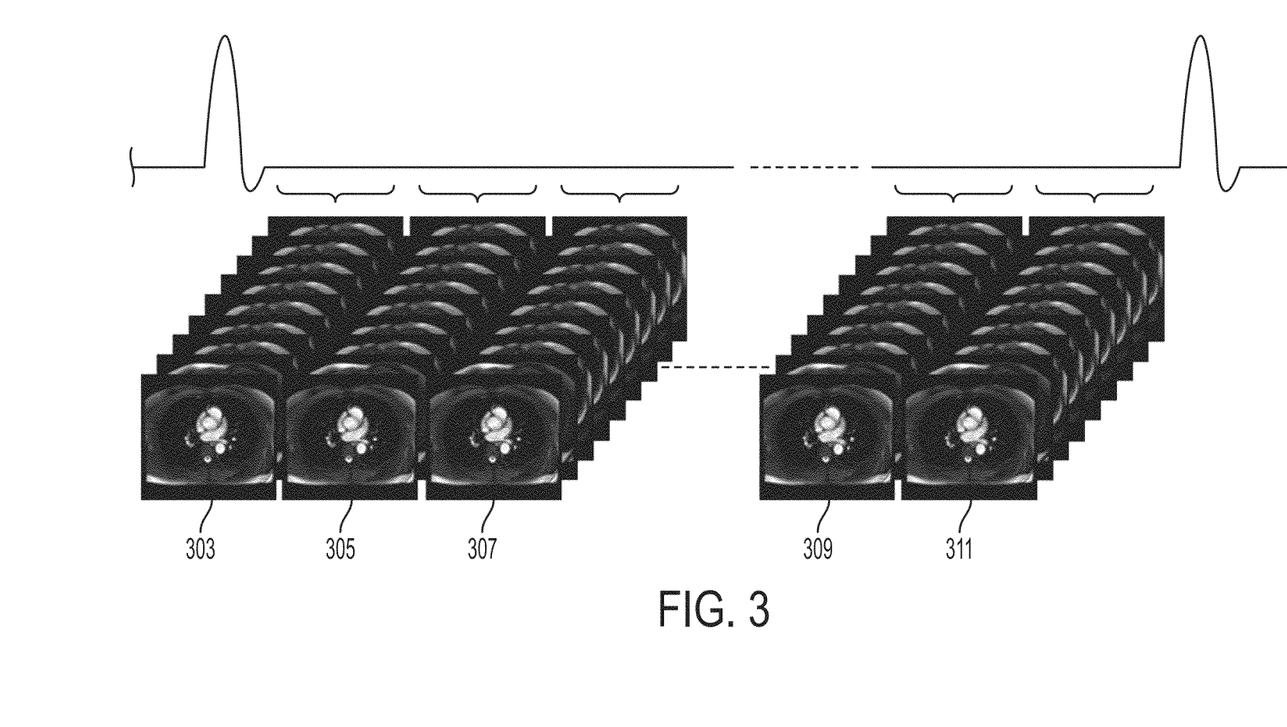
FIG. 3 shows 4D (3D cine or stack of 2D cine) images being used to derive information for automatic scan planning, according to invention principles.

FIG. 3 shows 4D (3D cine or 2D cine) images being used to derive information for automatic scan planning System 10 automates view planning in cardiac imaging, field-of-view calculation and optimal timing parameter selection by optimized selection of parameters for specific patient and imaging views. Specifically, system 10 in one embodiment employs a method involving acquiring 4D images 303, 305, 307-309, 311 covering an entire heart over a cardiac cycle. System 10 acquires the images as a 3D cine or a stack of 2D cine slices. The system 10 method further involves automatic selection of a reference volume (e.g. comprising image data at a particular cardiac phase) for segmentation. The image data processor in computer 28 performs segmentation of the heart from an imaging volume derived for a particular cardiac phase. The use of an imaging volume acquired at a diastolic phase is shown herein, since most subsequent cardiac scans for morphology, tissue characterization, and angiography are acquired during a mid-diastole phase.

Figure 4:
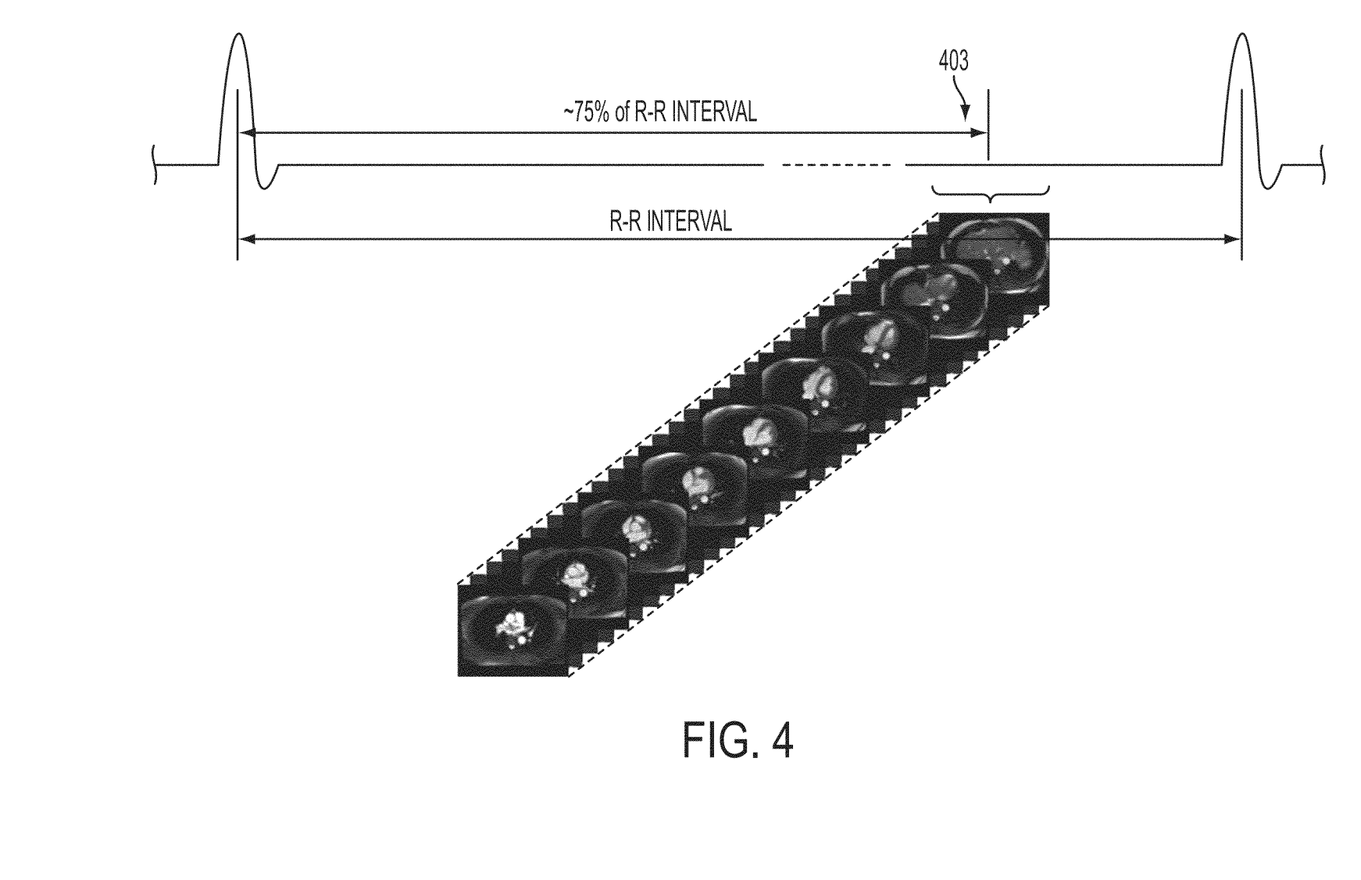
FIG. 4 shows a reference volume being automatically selected, e.g., a 3D volume in mid-diastole cardiac phase (close to 75% of the R-R interval) for subsequent processing, according to invention principles.

FIG. 4 shows a reference volume being automatically selected by the image data processor, e.g., a 3D volume in mid-diastole cardiac phase (close to 75% of the R-R interval) for subsequent processing. Although not being patient specific, known previous whole-heart studies from dual-source Computed Tomography, for example, indicate an overall optimal reconstruction window is substantially 75% of an R-R interval in patients. For the purposes of the present disclosure, the term "substantially 75%" of an R-R interval refers to an overall optimal reconstruction window that is between 70% and 80% of an R-R interval." An imaging volume substantially 75% 403 of the R-R interval is used as a reference frame for subsequent automatically performed steps of the system 10 method for view planning, field-of-view calculation and optimal timing parameter selection. Timing parameter selection is refined in subsequent steps of the method.

Figure 5:
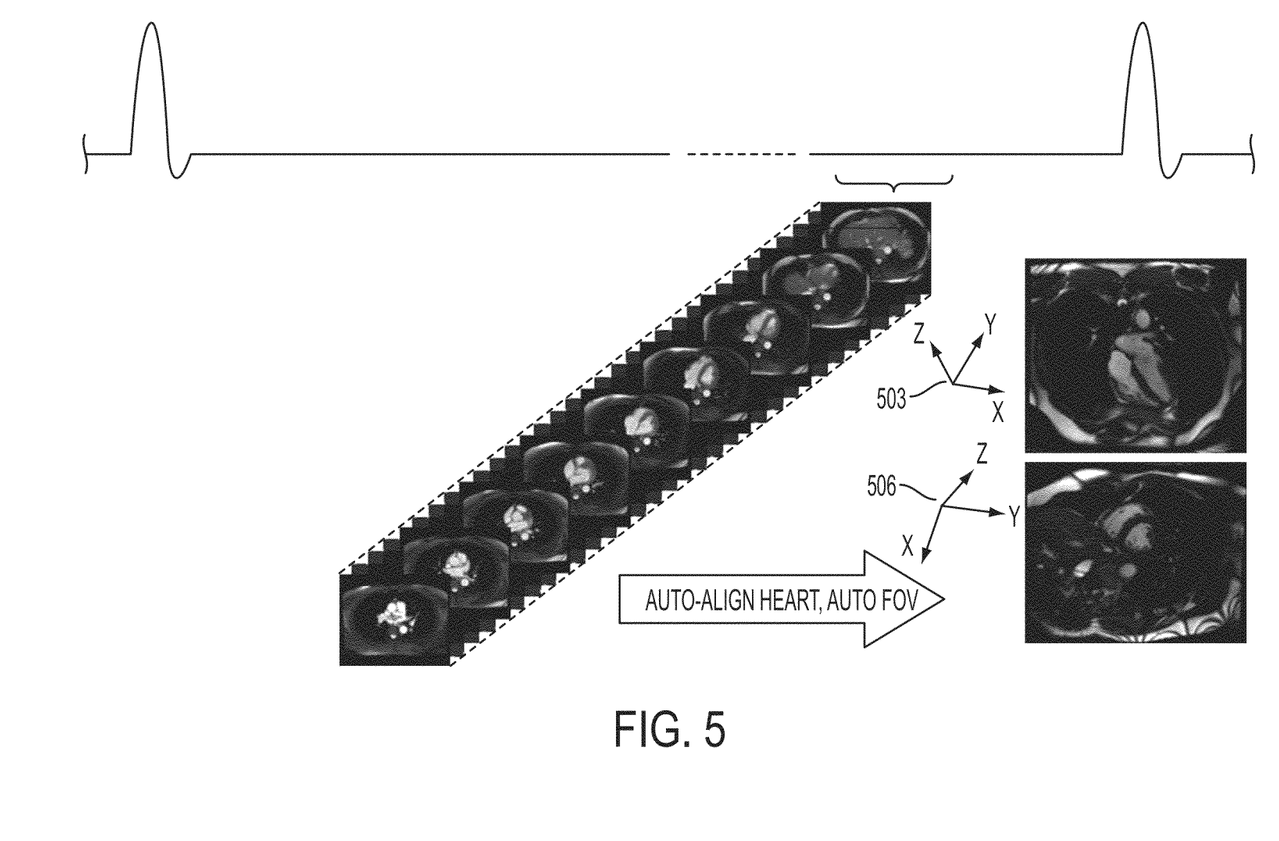
FIG. 5 shows system automatic determination of cardiac views (e.g., 4-chamber, 3-chamber, 2-chamber views) and an imaging field-of-view and determination of coordinate and normal vectors for the individual views, according to invention principles.

FIG. 5 shows automatic determination by the image data processor of cardiac views (e.g., 4-chamber, 3-chamber, 2-chamber views) and an imaging field-of-view and determination of coordinate and normal vectors for the individual views comprising the reference volume determined in connection with FIG. 4 and that will be used for subsequent scans. The image data processor in computer 28 calculates clinical cardiac views and an imaging field-of-view automatically and uses a known method to derive coordinate and normal vectors 503, 506 for clinical cardiac views calculated from the reference volume. A known method for deriving coordinate and normal vectors is described, for example, in "Method and System for Automatic View Planning for Cardiac Magnetic Resonance Imaging Acquisition", application Ser. No. 13/293,239, Publication number: US 2012/0121152, filed Nov. 10, 2011, or "Automatic Determination of Field of View In Cardiac MRI", application Ser. No. 12/393,236; Publication number: US 2009/0290776, filed Feb. 26, 2009. The entirety of both application Ser. No. 13/293,239 and application Ser. No. 12/393,236 is hereby incorporated by reference.

Figure 6:
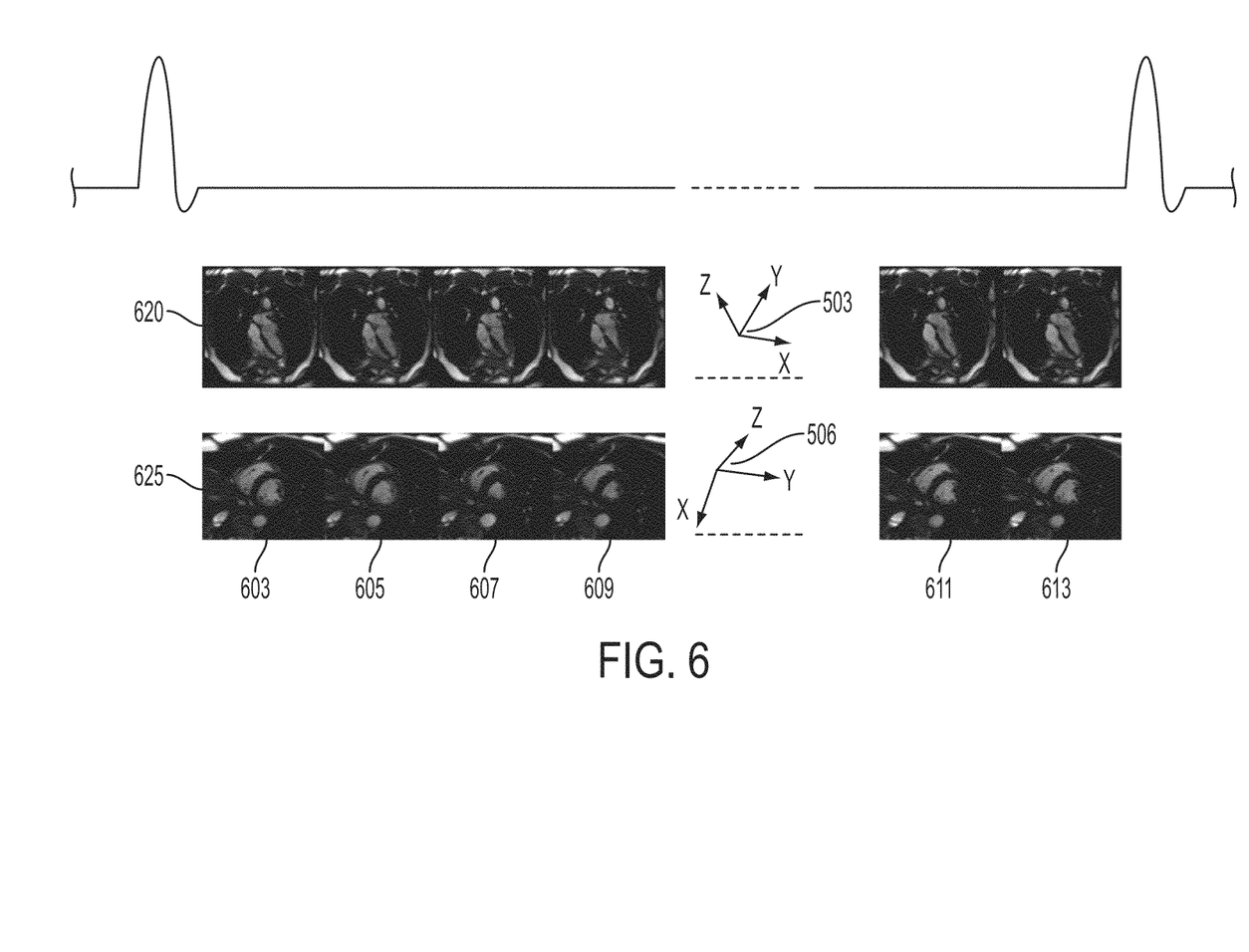
FIG. 6 shows propagation of calculated coordinate and normal information to remaining temporal volumes so that individual views are reformatted from volumetric data of each temporal phase, according to invention principles.

FIG. 6 shows propagation by the image data processor of calculated coordinate and normal information of the reference volume (coordinate and normal vectors 503, 506 FIG. 5) determined for the reference volume (at 75% of the RR interval) to remaining temporal phase volumes 603, 605, 607, 609, 611 and 613 of four chamber (row 620) and short axis (row 625) views so that the individual views are reformatted from volumetric data of each temporal phase. This step enables automated imaging determination for subsequent imaging to be performed at any phase in the cardiac cycle.

Figure 7:
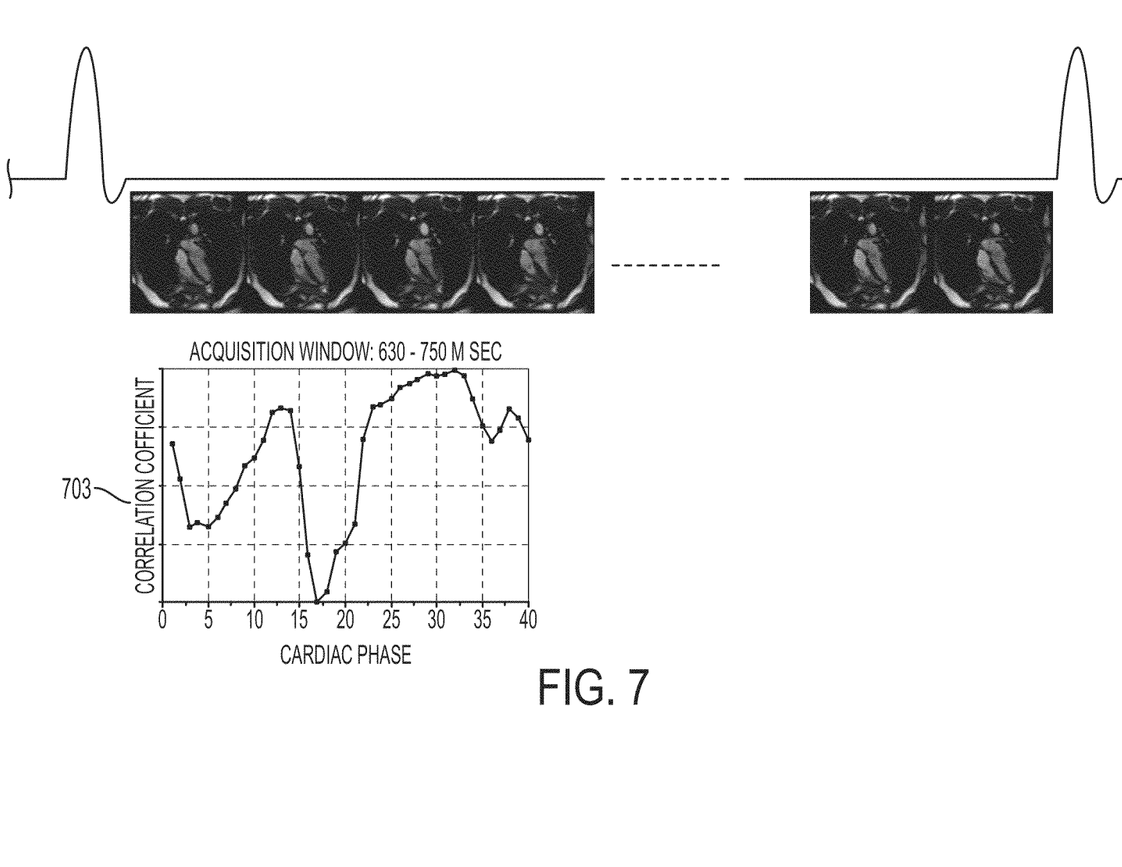
FIG. 7 shows for each individual view, system combination of images of different cardiac phases and analysis of each cine image series to derive view-specific motion-time information in order to identify a time period with minimal cardiac motion, according to invention principles.

FIG. 7 shows for each individual view, combination by the image data processor of images of different cardiac phases and analysis of each cine image series to derive view-specific motion-time information in order to identify a time period with minimal cardiac motion. For each individual cardiac view, the image data processor combines images calculated from each temporal volume to form a cine image series. Cine images from each view may be used for deriving view-specific motion information as a function of trigger time. For instance, in one embodiment, cross-correlation between successive cardiac phases is calculated as an indication of cardiac motion. Cardiac phases with cross-correlation coefficient (CC) above a threshold ($\alpha$) may be used to guide subsequent orientation-specific timing settings. For instance, cardiac phases fulfilling $CC_i > (CCmax - \alpha \cdot (CCmax - CCmin))$ are used in one embodiment. Selection of threshold (a) is application specific and is predetermined to facilitate the automation of trigger time calculation. For angiographic applications (e.g., coronary lumen or coronary wall imaging), it is determined that $\alpha = 0.05$ is substantially optimal to achieve good motion control as well as reasonable imaging time and effective fat saturation.

The image data processor calculates correlation coefficient between image pairs of successive cardiac phases. Specifically, the image data processor determines correlation of successive image pairs of a four chamber view as illustrated in graph 703 showing a plot of cross correlation (y axis) of successive image pairs against phase number (x axis) where a heart cycle has 40 cardiac phases. Thereby the image data processor calculates view-specific (four-chamber in this case) motion-time information. In this figure correlation coefficient between successive cardiac phases is calculated. For this patient, cardiac phase number 28 to 33 were identified as diastasis (minimal cardiac motion), corresponding to an optimally timed acquisition window from 630 to 750 msec. The image data processor in computer 28 stores calculated cardiac views, field-of-view and optimal timing parameters in the repository in computer 28 for use during an imaging examination. The image data processor automatically optimizes and stores parameter settings for subsequent measurements for cardiac morphology, tissue characterization, angiography and other applications for optimal timing selection.

For each individual view, the image data processor combines images of phases and analyze each cine image series to derive view-specific motion information as a function of trigger time in order to identify a time period with minimal cardiac motion. A repository of data in computer 28 associates, for acquisition of an image in a particular heart phase, different image orientations, different patient heart rates or ranges and different image volumes of interest, with corresponding different data items identifying respective corresponding particular acquisition points within an individual heart cycle relative to a start point of the heart cycle.

Table 1 shows association of different patient heart rate ranges with corresponding different data items identifying respective corresponding particular acquisition points within an individual heart cycle relative to a start point of the heart cycle (percentage of an RR cycle from start of the RR cycle). Patients with slow heart rate tend to have a quiescent period (with less heart motion) during mid-diastole. However, in patients with increased heart rate, such a quiescent period is better observed in late-systole of a heartbeat. The data for a particular patient identifying different patient heart rate ranges with respective corresponding particular acquisition points within an individual heart cycle relative to a start point of the heart cycle may be empirically determined for the patient concerned.

TABLE 1

Timing selection based on heart rate.

| Heart rate (beats/minute) | Optimal timing (with reference to RR interval) |
|---|---|
| >65 | 40% |
| <=65 | 75% |

Table 2 shows association of different image orientations with corresponding different data items identifying respective corresponding particular acquisition points within an individual heart cycle relative to a start point of the heart cycle (time range from start of the RR cycle). The right heart has more motion relative to the left heart. Therefore a shorter time duration is used for imaging the right heart (for example, right coronary artery) in comparison to the left heart (for example, left anterior coronary artery).

TABLE 2

Timing selection based on imaging orientation of interest.

| Imaging orientation of interest | Optimal duration for imaging data readout |
| --- | --- |
| Left heart | 100-150 msec |
| Right heart | 80-120 msec |

Table 3 shows association of different image volumes of interest with corresponding different data items identifying respective corresponding particular acquisition points within an individual heart cycle relative to a start point of the heart cycle (time range from start of the RR cycle). The system determines an optimized imaging protocol timing for cardiac imaging in response to the recognition that there is a shorter quiescent period in the atrium compared to a ventricle of the heart, for example.

TABLE 3

Timing selection based on imaging volume in the heart.

| Imaging volume of interest | Optimal duration for imaging data readout |
| --- | --- |
| Heart atrium | 60-80 msec |
| Heart ventricle | 100-120 msec |

Returning to FIG. 1, central control unit 26 uses information stored in an internal database to process the detected MR signals in a coordinated manner to generate high quality images of a selected slice (or slices) of the body and adjusts other parameters of system 10. The stored information comprises predetermined pulse sequence and magnetic field gradient and strength data as well as data indicating timing, orientation and spatial volume of gradient magnetic fields to be applied in imaging. Generated images are presented on display 40. Computer 28 includes a graphical user interface (GUI) enabling user interaction with central controller 26 and enables user modification of magnetic resonance imaging signals in substantially real time. Display processor 37 processes the magnetic resonance signals to provide image representative data for display on display 40, for example.

Figure 8:
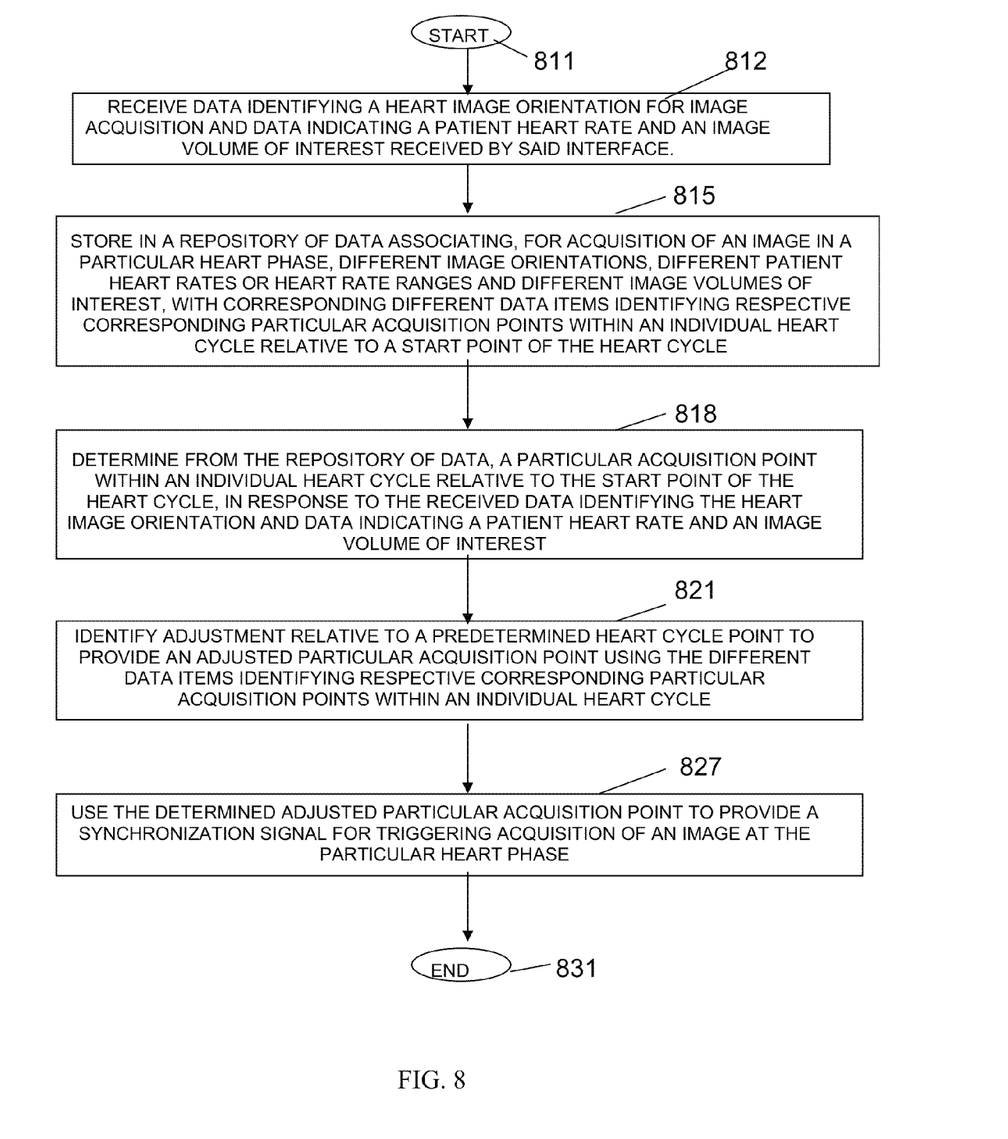
FIG. 8 shows a flowchart of a process performed by an imaging system for automatic determination of a cardiac timing parameter for acquiring a cardiac image in a desired heart phase, according to invention principles.

FIG. 8 shows a flowchart of an MR (Magnetic Resonance) method performed by system 10 (FIG. 1) for automatic determination of a cardiac timing parameter for acquiring a cardiac image in a desired heart phase. In step 812 following the start 811, an interface in at least one processing device (e.g. computer 28) in system 10 receives data identifying a heart image orientation for image acquisition, data indicating a patient heart rate and an image volume of interest. In one embodiment, the different image orientations include: (a) a short-axis orientation, (b) a four-chamber orientation, (c) a three-chamber orientation, (d) a two-chamber orientation, (e) a left heart orientation, and (e) a right heart orientation. The different image volumes of interest comprise a heart atrium and a heart ventricle and the different patient heart rate ranges comprise below and above 65 beats per minute, for example.

In step 815 the at least one processing device stores in repository 17 data associating, for acquisition of an image in a particular heart phase, different image orientations, data indicating a patient heart rate and an image volume of interest, with corresponding different data items identifying respective corresponding particular acquisition points within an individual heart cycle relative to a start point of the heart cycle. In one embodiment, the particular heart phase is selected from at least one of, (a) an end-of-systole phase and (b) a mid-of-diastole phase. The at least one processing device in step 818 determines from the repository of data, a particular acquisition point within an individual heart cycle relative to the start point of the heart cycle by in one embodiment identifying adjustments relative to a predetermined heart cycle point, in response to the received data identifying the heart image orientation and received data indicating a patient heart rate and an image volume of interest.

In step 821 the at least one processing device identifies adjustment relative to a predetermined heart cycle point to provide an adjusted particular acquisition point using the different data items identifying respective corresponding particular acquisition points within an individual heart cycle. In one embodiment, the predetermined heart cycle point comprises a point at substantially 75% of a heart cycle between successive ECG R-waves. The at least one processing device in step 827 uses the determined adjusted particular acquisition point to provide a synchronization signal for triggering acquisition of an image at the particular heart phase. The process of FIG. 8 terminates at step 831.

Figure 9:
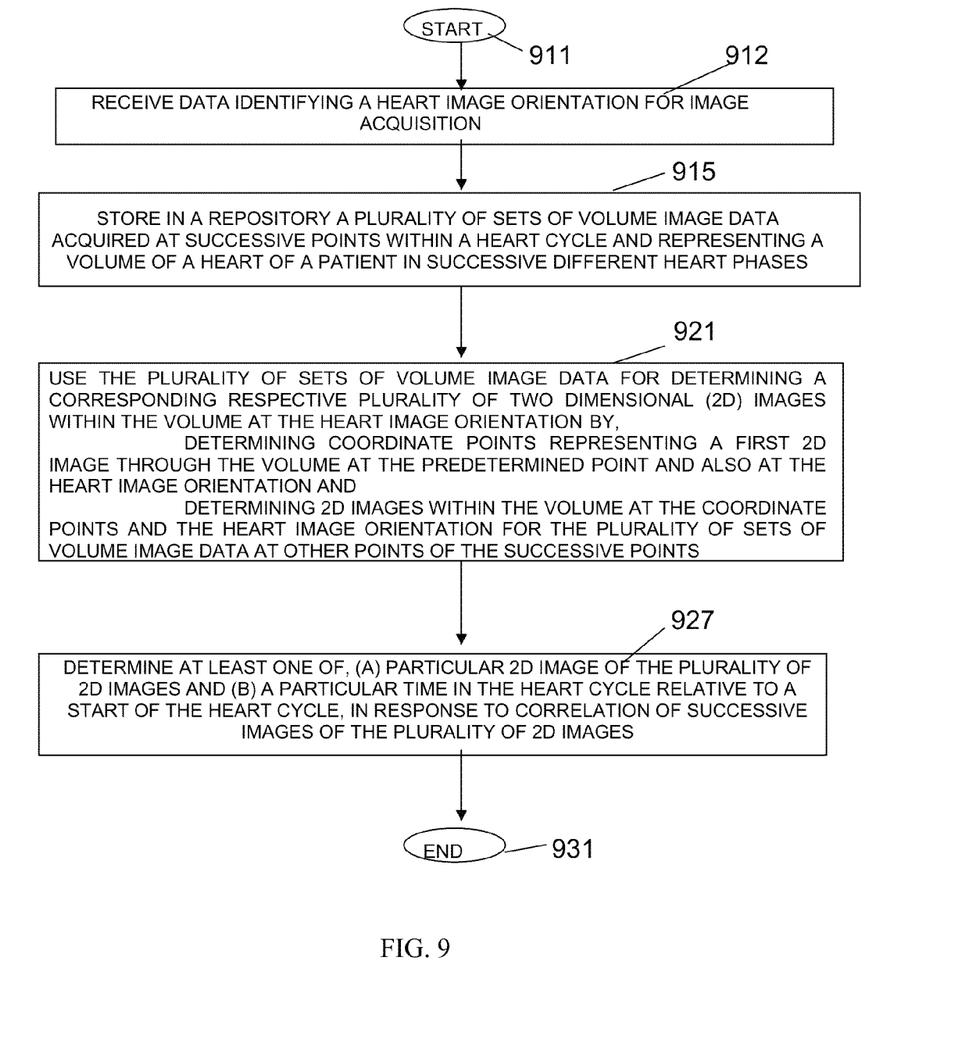
FIG. 9 shows a flowchart of a process performed by an imaging system for automatic determination of a time in a cardiac cycle for acquiring a cardiac image in a desired heart phase, according to invention principles.

FIG. 9 shows a flowchart of a process performed by system 10 (FIG. 1) for automatic determination of a time in a cardiac cycle for acquiring a cardiac image in a desired heart phase. In step 912 following the start 911, an interface in at least one processing device in system 10 receives data identifying a heart image orientation for image acquisition, data indicating a patient heart rate and an image volume of interest. In one embodiment, the different image orientations include: (a) a short-axis orientation, (b) a four-chamber orientation, (c) a three-chamber orientation, (d) a two-chamber orientation, (e) a left heart orientation, and (e) a right heart orientation.

In step 915 the at least one processing device stores in repository 17 a plurality of sets of volume image data acquired at successive points within a heart cycle and representing a volume of a heart of a patient in successive different heart phases. The successive points include a predetermined point within the heart cycle. In one embodiment, the predetermined heart cycle point comprises a point at substantially 75% of the heart cycle between successive ECG R-waves. In an embodiment, the particular heart phase is selected from at least one of, (a) an end-of-systole phase and (b) a mid-of-diastole phase. In step 921, an image data processor in the at least one processing device uses the plurality of sets of volume image data for determining a corresponding respective plurality of two dimensional (2D) images within the volume at the heart image orientation. The image data processor determines the corresponding respective plurality of 2D images by, determining coordinate points representing a first 2D image through the volume at the predetermined point and also at the heart image orientation and determining 2D images within the volume at the coordinate points and the heart image orientation for the plurality of sets of volume image data at other points of the successive points.

In step 927 the image data processor determines at least one of, (a) particular 2D image of the plurality of 2D images and (b) a particular time in the heart cycle relative to a start of the heart cycle, in response to correlation of successive images of the plurality of 2D images. The particular 2D image of the plurality of 2D images and the particular time in the heart cycle, correspond to a particular heart cycle phase within the heart cycle. In one embodiment, the image data processor determines at least one of, (a) particular 2D image of the plurality of 2D images corresponding to the end-of-systole phase and (b) a particular time in the heart cycle relative to a start of the heart cycle corresponding to the end-of-systole phase, in response to substantially minimizing correlation of luminance content of the successive images of the plurality of 2D images. In another embodiment, the image data processor determines at least one of, (a) particular 2D image of the plurality of 2D images corresponding to the mid-of-diastole phase and (b) a particular time in the heart cycle relative to a start of the heart cycle corresponding to the end-of-diastole phase, in response to substantially maximizing correlation of luminance content of the successive images of the plurality of 2D images. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

DEFINITIONS

EPI=Echo planar imaging involves image acquisition whereby a complete image is formed from a single data sample (k-space lines are acquired in one repetition time) of a gradient echo or spin echo sequence.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

TI comprises inversion time, the time between an inversion recovery pulse and the next RF excitation pulse. TI determines the image contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

FA comprises flip angle, i.e., an RF flip angle. For an inversion pulse, FA=180 degrees.

A saturation pulse (or saturation recovery pulse) comprises an RF pulse, typically 90 degrees (or any odd multiple of 90 degrees). Some systems use a spoiler gradient after the RF pulse. In a particular type of partial saturation pulse sequence a preceding pulse leaves the spins in a state of saturation, so that recovery at the time of the next pulse has taken place from an initial condition of no magnetization.

Spoiler gradient=a magnetic field gradient pulse applied to effectively remove transverse magnetization of a field coil by producing a rapid variation of its phase along the direction of the gradient. For the T2prep module it is played after the 90 degrees flip back (also known as tip up) pulse has been played. It destroys remaining transverse magnetization so that after playing the entire T2prep module magnetization is again in the longitudinal direction.

Segmented data acquisition records the different parts of raw data space (the segments) in a periodic fashion by repeatedly playing out a pulse sequence comprising an inversion pulse sequence and MR data acquisition pulses and acquiring a different set of k-space lines during readout (acquisition).

B0 is the main static base MRI magnetic field.

B1 is the RF transmit coil field.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The MR imaging system automates selection of patient-specific, orientation and volume of interest, dependent optimal timing parameters in order to achieve consistent, operator-independent image quality with minimal motion artifacts in cardiac imaging and automates selection of scanning views and imaging field-of-view, in providing automated cardiac scans. Further, the processes and applications may, in alternative embodiments, be located on one or more (e.g., distributed) processing devices on a network linking the units of FIG. 1. Any of the functions and steps provided in FIGS. 1-9 may be implemented in hardware, software or a combination of both. No claim element herein is to be construed under the provisions of 35 U.S.C. 112, sixth paragraph, unless the element is expressly recited using the phrase "means for."

What is claimed is:

1. An MR (Magnetic Resonance) imaging system for acquiring a cardiac image in a heart phase, the system comprising:
    an interface for receiving data identifying a heart image orientation for image acquisition;
    a repository of data associating, for acquisition of an image in a particular heart phase, different image orientations with corresponding different data items identifying respective corresponding particular acquisition points within an individual heart cycle relative to a start point of said heart cycle; and
    an acquisition timing processor configured to:
        determine from said repository of data, a particular acquisition point within an individual heart cycle relative to said start point of said heart cycle, in response to the received data identifying said heart image orientation,
        identify adjustment relative to a predetermined heart cycle point to provide an adjusted particular acquisition point using said different data items identifying respective corresponding articular acquisition points within an individual heart cycle, and
        use the adjusted particular acquisition point to provide a synchronization signal for triggering acquisition of said image at said particular heart phase.

2. The system according to claim 1, wherein
said different image orientations include, (a) a short-axis orientation, (b) a four-chamber orientation, (c) a three-chamber orientation and (d) a two-chamber orientation.

3. The system according to claim 1, wherein
said particular heart phase is selected from at least one of, (a) an end-of-systole phase and (b) a mid-of-diastole phase.

4. The system according to claim 1, wherein
said different data items identify respective corresponding particular acquisition points within an individual heart cycle by identifying adjustments relative to a predetermined heart cycle point.

5. The system according to claim 1, wherein
said particular acquisition point comprises a point at substantially 75% of said heart cycle between successive ECG R-waves.

6. The system according to claim 1, wherein
said repository of data associates different image orientations and at least one of, (a) different patient heart rates or heart rate ranges and (b) different image volumes of interest, with corresponding different data items identifying respective corresponding particular acquisition points within an individual heart cycle relative to a start point of said heart cycle, in response to data indicating a patient heart rate and an image volume of interest received by said interface.

7. An MR (Magnetic Resonance) imaging system for acquiring a cardiac image in a heart phase, comprising:
    an interface for receiving data identifying a heart image orientation for image acquisition and a patient heart rate;
    a repository of data associating, for acquisition of an image in a particular heart phase, different image orientations and different patient heart rates or heart rate ranges, with corresponding different data items identifying respective corresponding particular acquisition points within an individual heart cycle relative to a start point of said heart cycle; and
    an acquisition timing processor configured to:
        determine from said repository of data, a particular acquisition point within an individual heart cycle relative to said start point of said heart cycle, in response to the received data identifying said heart image orientation and patient heart rate,
        identify adjustment relative to a predetermined heart cycle point to provide an adjusted particular acquisition point using said different data items identifying respective corresponding particular acquisition points within an individual heart cycle, and
        use the adjusted particular acquisition point to provide a synchronization signal for triggering acquisition of said image at said particular heart phase.

8. The system according to claim 7, wherein
said repository of data associates different image volumes of interest, with corresponding different data items identifying respective corresponding particular acquisition points within an individual heart cycle relative to a start point of said heart cycle.

9. The system according to claim 8, wherein
said different image volumes of interest comprise a heart atrium and a heart ventricle.

10. The system according to claim 7, wherein
said different image orientations include, (a) a short-axis orientation, (b) a four-chamber orientation, (c) a three-chamber orientation (d) a two-chamber orientation, (e) a left heart orientation and (e) a right heart orientation.

11. The system according to claim 7, wherein
said particular heart phase is selected from at least one of, (a) an end-of-systole phase and (b) a mid-of-diastole phase.

12. An MR (Magnetic Resonance) imaging method for acquiring a cardiac image in a heart phase, the method comprising:
    receiving data identifying a heart image orientation for image acquisition;
    storing in a repository of data associating, for acquisition of an image in a particular heart phase, different image orientations with corresponding different data items identifying respective corresponding particular acquisition points within an individual heart cycle relative to a start point of said heart cycle;
    determining from said repository of data, a particular acquisition point within an individual heart cycle relative to said start point of said heart cycle, in response to the received data identifying said heart image orientation; and
    identifying adjustment relative to a predetermined heart cycle point to provide an adjusted particular acquisition point using said different data items identifying respective corresponding particular acquisition points within an individual heart cycle; and
    using the adjusted particular acquisition point to provide a synchronization signal for triggering acquisition of said image at said particular heart phase.

13. The method of claim 12, further comprising:
storing in said repository data associating at least one of,
(a) different patient heart rates or heart rate ranges and
(b) different image volumes of interest, with corresponding different data items identifying respective corresponding particular acquisition points within an individual heart cycle relative to a start point of said heart cycle.

14. The method of claim 13, wherein
said different image orientations include, (a) a short-axis orientation, (b) a four-chamber orientation, (c) a three-chamber orientation (d) a two-chamber orientation, (e) a left heart orientation and (e) a right heart orientation, and
said different image volumes of interest comprise a heart atrium and a heart ventricle.

* * * * *